US010869494B2

(12) United States Patent
Fujihara et al.

(10) Patent No.: US 10,869,494 B2
(45) Date of Patent: Dec. 22, 2020

(54) SWEETENER CONTAINING D-PSICOSE AND FOODS AND DRINKS OBTAINED BY USING THE SAME

(75) Inventors: Hideki Fujihara, Itami (JP); Kazuhiro Okuma, Itami (JP); Tetsuo Iida, Itami (JP); Ken Izumori, Kita-gun (JP); Masaaki Tokuda, Kita-gun (JP); Kazuhiro Fukada, Kagawa (JP)

(73) Assignee: MATSUTANI CHEMICAL INDUSTRY CO., LTD., Itami (JP)

( * ) Notice: Subject to any disclaimer, the term of this patent is extended or adjusted under 35 U.S.C. 154(b) by 420 days.

(21) Appl. No.: 12/514,216

(22) PCT Filed: Mar. 26, 2007

(86) PCT No.: PCT/JP2007/056166
§ 371 (c)(1),
(2), (4) Date: May 8, 2009

(87) PCT Pub. No.: WO2008/059623
PCT Pub. Date: May 22, 2008

(65) Prior Publication Data
US 2009/0304891 A1 Dec. 10, 2009

(30) Foreign Application Priority Data
Nov. 10, 2006 (JP) ................. 2006-305816

(51) Int. Cl.
| | | |
|---|---|---|
| A23L 27/30 | (2016.01) | |
| A61K 8/60 | (2006.01) | |
| A23L 2/60 | (2006.01) | |
| A23C 9/13 | (2006.01) | |
| A61Q 11/00 | (2006.01) | |
| A23G 4/06 | (2006.01) | |
| A23G 4/10 | (2006.01) | |
| A23G 3/42 | (2006.01) | |
| A23G 3/36 | (2006.01) | |
| A61K 47/26 | (2006.01) | |

(52) U.S. Cl.
CPC ............... *A23L 27/33* (2016.08); *A23C 9/13* (2013.01); *A23G 3/36* (2013.01); *A23G 3/42* (2013.01); *A23G 4/06* (2013.01); *A23G 4/10* (2013.01); *A23L 2/60* (2013.01); *A23L 27/34* (2016.08); *A23L 27/36* (2016.08); *A61K 8/60* (2013.01); *A61Q 11/00* (2013.01); *A61K 47/26* (2013.01)

(58) Field of Classification Search
CPC .......... A23L 1/236; A23L 1/2363; A23L 2/60; A23L 27/33; A23L 27/36
USPC ...................................... 426/548
See application file for complete search history.

(56) References Cited

U.S. PATENT DOCUMENTS

| 4,262,032 | A | 4/1981 | Levin | |
|---|---|---|---|---|
| 5,679,562 | A * | 10/1997 | Izumori | C12N 9/90 |
| | | | | 435/183 |
| 6,432,464 | B1 * | 8/2002 | Andersen et al. | 426/548 |
| 7,147,883 | B1 | 12/2006 | Silver | |
| 7,186,431 | B1 | 3/2007 | Silver | |
| 2002/0004092 | A1 | 1/2002 | Riha et al. | |
| 2002/0160090 | A1 * | 10/2002 | Lee et al. | 426/548 |
| 2002/0187232 | A1 | 12/2002 | Lee et al. | |
| 2002/0197371 | A1 * | 12/2002 | Lee et al. | 426/548 |
| 2005/0106305 | A1 * | 5/2005 | Abraham et al. | 426/590 |
| 2006/0134292 | A1 * | 6/2006 | Abelyan | A23L 1/2366 |
| | | | | 426/548 |
| 2007/0003679 | A1 * | 1/2007 | Shimizu et al. | 426/548 |
| 2007/0116828 | A1 | 5/2007 | Prakash et al. | |
| 2007/0116834 | A1 | 5/2007 | Prakash et al. | |
| 2007/0275147 | A1 | 11/2007 | Prakash et al. | |
| 2010/0166678 | A1 * | 7/2010 | Iida | A61K 8/60 |
| | | | | 424/49 |

FOREIGN PATENT DOCUMENTS

| JP | 8-166164 A | 3/1996 |
|---|---|---|
| JP | 2001-11090 A | 1/2001 |

(Continued)

OTHER PUBLICATIONS

Yoshihara, K., Shinohara, Y., Hirotsu, T., Izumori, K., "Bioconversion of D-Psicose to D-Tagatose and D-Talitol by Mucoraceae Fungi," Journal of Bioscience and Bioengineering, vol. 101, No. 3, (2006) 219-222, available online as of May 20, 2006 at http://www.sciencedirect.com/science/article/pii/S1389172306705692.*
Schiffman, S. S., Booth, B. J., Carr, B. T., Losee, M. L., Sattely-Miller, E. A., and Graham, B. G., "Investigation of Synergism in Binary Mixtures of Sweeteners", Brain Research Bulletin, vol. 38, No. 2, pp. 105-120 (1995).*
Matsuo, T., Suzuki, H., Hashiguchi, M., and Izumori, K., "D-Psicose Is a Rare Sugar That Provides No Energy to Growing Rats," J. Nutr. Sci. Vitaminol., 48:77-80 (2002).*
International Search Report of PCT/JP2007/056166, dated May 1, 2007.

(Continued)

*Primary Examiner* — Jeffrey P Mornhinweg
(74) *Attorney, Agent, or Firm* — Westerman, Hattori, Daniels & Adrian, LLP

(57) ABSTRACT

Providing a D-psicose-containing sweetener with the modification of the taste of D-psicose, comprising D-psicose, a sugar alcohol and/or a high intensity sweetener, preferably containing D-psicose as the main component, particularly a low-calorie sweetener and/or a sweetener giving refreshing feel in the oral cavity, as well as foods and drinks obtained by using the D-psicose-containing sweetener with the modification of the taste of D-psicose, and other products given with sweetness. The sugar alcohol is one or more sugar alcohols selected from the group consisting of sorbitol, mannitol, lactitol, maltitol, xylitol and erythritol, while the high intensity sweetener is one or more high intensity sweeteners as selected from aspartame, acesulfame K, sodium cyclamate, sodium saccharin, Sucralose (under trade name), stevia sweetener, dulcin, taumatin, neotame and monellin.

8 Claims, No Drawings

(56) References Cited

FOREIGN PATENT DOCUMENTS

| JP | 2001-333729 A | 12/2001 | |
|---|---|---|---|
| JP | 2005213227 | * 8/2005 | ......... A61K 31/7004 |
| JP | 2005-263744 A | 9/2005 | |
| WO | 20021087358 A1 | 11/2002 | |

OTHER PUBLICATIONS

Nahon, D.F. et al, "Sensory Evaluation of Mixtures of Maltitol or Aspartame, Sucrose and an Orange Aroma." Chem. Senses, 1998, vol. 23, No. 1, pp. 59-66.
Saulo, A.A. et al, "Sugars and Sweetners in Foods", Food Safety and Technology, 2005, vol. 16, pp. 1-7.
Third Party Observactions dated Apr. 5, 2017, issued in counterpart European Application No. 07739604.2. (12 pages).

* cited by examiner

SWEETENER CONTAINING D-PSICOSE AND FOODS AND DRINKS OBTAINED BY USING THE SAME

TECHNICAL FIELD

The present invention relates to a D-psicose-containing sweetener with the modification of the taste of D-psicose, comprising a combination of D-psicose, a sugar alcohol and/or a high intensity sweetener. More specifically, the invention relates to a low-calorie sweetener, a sweetener giving refreshing feel in the oral cavity as well as foods and drinks and the like obtained by using the same.

BACKGROUND ART

Sucrose is a sweetener of good sweetness quality and is popular in a great number of people. In recent years, however, it has been noted that excess intake of sucrose causes obesity and various lifestyle-related diseases. In such circumstance, low-calorie sweeteners have been developed from the standpoint of health-oriented minds.

D-Psicose is contained at an extremely small amount in molasses and isomerized sugars and is one of rare sugars enzymatically producible from D-fructose with epimerase. It is expected that D-psicose may be applicable to various foods, because D-psicose has physiological functions such as anti-oxidative property and has almost zero-kilocalorie energy although D-psicose is at a sweetness level of 60 to 70% of the sweetness level of sucrose and because D-psicose is highly soluble. In case of using D-psicose as a sweetener for foods, D-psicose is used at a large amount when intending to give sweetness at a needed level to a food, so that the resulting food gets too much heavy taste, and additionally the start of the sweetness of D-psicose is just slow. Thus, the use of D-psicose alone is not practical.

Alternatively, sugar alcohols and high intensity sweeteners contain very low calories, and are used as sweeteners as alternative sucrose. Compared with sucrose, however, the taste of sugar alcohols in a first stage of ingestion may sometimes be too sharp or the aftertaste thereof may sometimes be unfavorable.

Because a high intensity sweetener having sweetness about several hundred folds or more that of sucrose can exert the intended sweetness even when added at a small amount, such sweetener is used as a low-calorie sweetener. However, the sweetness of such sweetener may sometimes too slowly start or such sweetener has unique bitterness, disadvantageously. Hence, the use of such sweetener alone is not common but generally, such sweetener is used in combination. High intensity sweeteners, for example, aspartame, acesulfame K and Sucralose (under trade name) are widely used as sweeteners in diet foods and drinks, owing to the high sweetness ratio. However, consumers have got used to the taste of so-called regular products using sucrose, isomerized sugars for long years. Some of consumers are disagreeable with the taste of foods using the high intensity sweeteners. Concerning these three types of the high intensity sweeteners, various investigations have been made mainly about a combined use thereof with trehalose and erythritol (patent reference 1), a combined use thereof with dietary fiber (patent reference 2) or a combined use thereof with α-glycosylated stevia extract (patent reference 3). Currently, however, the resulting tastes have not yet satisfied consumers having got used to the taste of sucrose, isomerized sugars.

Patent reference 1: JP-A-2002-51723
Patent reference 2: JP-A-2004-41118
Patent reference 3: JP-A-2002-34501

DISCLOSURE OF THE INVENTION

Problems that the Invention is to Solve

It is a very important issue to develop a measure for reducing the intake of sucrose as one of major caloric sources and as an important sweetener for cooking and to develop a sweetener as an alternative sucrose, which is at a low calorie and gives taste comparable to that of sucrose.

Therefore, it is an object of the invention to provide a D-psicose-containing sweetener with the modification of the taste of D-psicose, particularly a low-calorie sweetener, by improving the problems of D-psicose, such as the slow start of the sweetness of D-psicose and the heavy taste through the use of D-psicose at a large amount to modify the taste so that the resulting sweetener can widely be used in foods and drinks like sucrose. It is an object of the invention to provide a D-psicose-containing sweetener with the modification of the taste of D-psicose and with refreshing feel, particularly a low-calorie sweetener, by improving the problems of D-psicose, such as the slow start of the sweetness of D-psicose and the heavy taste through the use of D-psicose at a large amount without any reduction of the refreshing feel of D-psicose to modify the taste, so that the resulting sweetener can widely be used in foods and drinks like sucrose.

It is another object of the invention to provide a drink or a food with extremely favorite taste and controlled calories, using the D-psicose-containing sweetener with the modification of the taste of D-psicose, as well as other products given with sweetness.

Means for Solving the Problems

The inventors made investigations so as to solve the problems of the conventional techniques. Consequently, the inventors found that a combined use of D-psicose and a sugar alcohol and/or a high intensity sweetener could improve the slow start of the sweetness of D-psicose and could also compensate the drawbacks of the tastes specific to the sugar alcohol and the high intensity sweetener, so that excellent taste could be expressed. Thus, the invention has been achieved.

Specifically, the gist of the invention resides in a D-psicose-containing sweetener with the modification of the taste of D-psicose, particularly a low-calorie sweetener and/or a sweetener giving refreshing feel in the oral cavity, which comprise D-psicose, a sugar alcohol and/or a high intensity sweetener, which preferably contains D-psicose as the main component.

More specifically, the gist of the invention resides in a D-psicose-containing sweetener with the modification of the taste of D-psicose, particularly a low-calorie sweetener and/or a sweetener giving refreshing feel in the oral cavity, which comprise D-psicose, one or more sugar alcohols selected from the group consisting of sorbitol, mannitol, lactitol, maltitol, xylitol and erythritol, and/or one or more high intensity sweeteners as selected from the group consisting of aspartame, acesulfame K, sodium cyclamate, sodium saccharin, Sucralose (under trade name), stevia sweetener, dulcin, taumatin, neotame and monellin, which preferably contains D-psicose as the main component.

The gist of the invention resides in foods and drinks obtained by using the D-psicose-containing sweetener with the modification of the taste of D-psicose, as well as other products given with sweetness.

Advantages of the Invention

In accordance with the invention, a low-calorie sweetener with taste comparable to that of sucrose can be provided using D-psicose. By combining D-psicose, a sugar alcohol and/or a high intensity sweetener together, problems such as the slow start of the sweetness of D-psicose and the heavy taste thereof when used at a large amount can be improved to modify the taste, so that a low-calorie sweetener usable in a wide range of foods and drinks like sucrose can be provided.

By modifying the slow start of the sweetness of D-psicose and the heavy taste thereof when used at a large amount with no reduction of the refreshing taste of D-psicose to modify the taste, a D-psicose-containing sweetener, particularly a low-calorie sweetener can be provided, which has the modified taste and the refreshing feel and which can be used in a wide range of foods and drinks like sucrose.

In accordance with the invention, foods and drinks with extremely favorable taste and calorie control, as well as other products given with sweetness can be provided, using the D-psicose-containing sweetener with the modification of the taste of D-psicose. The low-calorie sweetener provided in accordance with the invention has appropriate sweet quality at good solubility and low calorie, so the low-calorie sweetener can be used in a wide range of foods and drinks including beverages, candies, cold confectionaries, yoghurt, and chocolate. Additionally, the low-calorie sweetener is suitable for giving sweetness to base materials of pharmaceutical products (for example, sugar-coated tablets) and quasi-pharmaceutical products.

Using the D-psicose-containing sweetener with the modification of the taste of D-psicose, in accordance with the invention, there can be provided foods and drinks with extremely favorable taste such as high refreshing feel and calorie control, as well as other products given with sweetness.

BEST MODE FOR CARRYING OUT THE INVENTION

The D-psicose-containing sweetener with the modification of the taste of D-psicose, particularly the low-calorie sweetener and/or the sweetener giving refreshing feel in the oral cavity are described below in specific embodiments.

1. A D-psicose-containing sweetener with the modification of the taste of D-psicose, comprising D-psicose and a sugar alcohol, particularly a low-calorie sweetener and/or a sweetener giving refreshing feel in the oral cavity.

2. A sweetener described above in 1, wherein the sugar alcohol is sorbitol, mannitol, lactitol, maltitol, xylitol, or erythritol, or two or more thereof in combination.

3. A D-psicose-containing sweetener with the modification of the taste of D-psicose, comprising D-psicose and a high intensity sweetener, particularly a low-calorie sweetener and/or a sweetener giving refreshing feel in the oral cavity.

4. A sweetener described above in 3, wherein the high intensity sweetener is aspartame, acesulfame K, sodium cyclamate, sodium saccharin, Sucralose, stevia sweetener, dulcin, taumatin, neotame, or monellin or two or more thereof in combination.

5. A D-psicose-containing sweetener with the modification of the taste of D-psicose, comprising D-psicose, a sugar alcohol and a high intensity sweetener, particularly a low-calorie sweetener and/or a sweetener giving refreshing feel in the oral cavity.

6. A sweetener described above in 5, wherein the sugar alcohol is sorbitol, mannitol, lactitol, maltitol, xylitol, or erythritol, or two or more thereof in combination and the high intensity sweetener is aspartame, acesulfame K, sodium cyclamate, sodium saccharin, Sucralose (under trade name), stevia sweetener, dulcin, taumatin, neotame, or monellin or two or more thereof in combination.

D-psicose referred to in accordance with the invention is produced enzymatically from D-fructose with epimerase, and may be completely purified or may contain an extremely small amount of impurities during the enzymatic production. Relatively readily, D-psicose is prepared by approaches using for example epimerase (see for example JP-A-6-125776). The resulting D-psicose solution is purified if necessary by methods for deproteination, decoloring and desalting, and is then concentrated, from which a syrup-like D-psicose product can be collected. By fractionation and purification by column chromatography, furthermore, a specimen at a purity as high as 99% or more can readily be obtained. Such D-psicose may be used as a monosaccharide as it is.

The sugar alcohol referred to in accordance with the invention means a polyhydric alcohol prepared by reducing the aldehyde and ketone groups in a sugar to convert these groups to primary and secondary alcohol groups, respectively, and includes reduced glutinous maltose syrup containing as the main ingredients erythritol, sorbitol, xylitol, arabitol, mannitol, maltitol, isomaltitol, lactitol, palatinit, and maltitol; maltitol syrup, reduced malto-oligosaccharide, and reduced isomalto-oligosaccharide. Herein, those sugar alcohols if they can exist in both D forms and L forms such as sorbitol and mannitol may include the D forms and L forms thereof unless otherwise stated, with no specific limitation to the forms.

Preferably, a sugar alcohol is used at an amount of 5 to 1,000 parts per 100 parts of D-psicose.

Within the range, the slow start of the sweetness in the former stage and the sweetness in the latter stage are in good balance. At 5 parts or less, the sweetness in the former stage is insufficient so that not any intended sweetener can be provided. At 1,000 parts or more, the unfavorable aftertaste of a sugar alcohol gets stronger. Thus, 30 to 300 parts are more preferable.

The high intensity sweetener means a sweetener with a sweetness level several tens-fold to several hundreds-fold that of sucrose, and includes for example aspartame, acesulfame K, sodium cyclamate, sodium saccharin, Sucralose (under trade name), stevia sweetener, dulcin, taumatin, neotame, and monellin.

The high intensity sweetener is used at an amount of 0.008 to 5 parts per 100 parts of D-psicose. Within the range, the start of the sweetness in the former stage and the sweetness in the latter stage are in good balance. At 0.008 parts or less, the sweetness in the former stage is insufficient, while at 5 parts or more, the bitterness of the sweetener at a sweetness level emerges or the after-sweetness is too strong, unfavorably. Still furthermore, 0.05 to 1.5 parts are preferable.

The form of the low-calorie sweetener of the invention may satisfactorily be any form such as solids for example powders, fine powders, granules, crystals, and tablets; aqueous solutions; and solutions. Further, the method for producing the same is not specifically limited. Without departing from the objects of the invention, furthermore, the low-calorie sweetener of the invention may contain other sweetness ingredients and those for use as fillers and carriers, which are not ingredients so as to give taste.

Additionally, D-psicose, a sugar alcohol and/or a high intensity sweetener may preliminarily be mixed together. In some case, however, these may separately be added. In conclusion, D-psicose, a sugar alcohol and/or a high intensity sweetener should concurrently exist in the final foods or drinks. Still further, the low-calorie sweetener of the invention may be used in combination with sweeteners conventionally used. In case that the low-calorie sweetener is used as a part of an alternative of caloric sucrose and fructose, for example, calorie reduction can be attained, and additionally, the resulting sweetness can be diversified via the combination of other sweeteners, to satisfy the preference.

In accordance with the invention, there are provided foods and drinks as well as other products given with sweetness, as obtained by using the D-psicose-containing sweetener with the modification of the taste of D-psicose, particularly the low-calorie sweetener and/or the sweetener giving refreshing feel in the oral cavity.

The foods and drinks referred to herein mean general foods requiring sweetness, such as drinks, candy, cold confectioneries, yoghurt, and chocolate. Additionally, the other products given with sweetness are products given with sweetness, such as pharmaceutical products, and oral compositions.

In other words, the D-psicose-containing sweetener with the modification of the taste of D-psicose, particularly the low-calorie sweetener and/or the sweetener giving refreshing feel in the oral cavity have got improvements in the problems of D-psicose, such as the slow start of the sweetness and the heavy taste due to the use thereof at a large amount, to modify the taste thereof, so that the sweeteners are in good harmonization with other types of taste of various substances, including sour taste, salty taste, stringency, "umami" and bitterness, like sucrose. Hence, the sweeteners can be used in a wide range of common foods and drinks so as to give sweetness thereto or improve the taste or the quality thereof.

The sweeteners can be used as sweeteners, taste modifiers and quality modifies for various seasonings for example soy sauce, powdery soy sauce, miso paste, powdery miso, unrefined sake (moromi), fermented seasoning (jyan), seasoned powders for sprinkling on rice, mayonnaise, dressings, edible vinegar, seasoned vinegar, powdery vinegar for sushi, Chinese seasoning mix, dip for tempura, noodle soup, sauce, ketchup, gravy for broiled meat, solid curry gravy, powdery or solid stew gravy, soup stock, Japanese soup seasoning mix, combined seasonings, mirin, new type-mirin, table sugar, and coffee sugar.

The sweeteners can be used as sweeteners, taste modifiers and quality modifiers for various drinks and foods, for example various Japanese-style confectioneries, such as rice cracker, very small rice biscuits, sweetened rice cracker, rice cake, buns wit bean-jam fillings, steamed mixture of rice powder, sugar and other powders (ui-ro), bean jams, sweet jellied adzuki-bean paste, water-enriched sweet jellied adzuki-bean paste, kingyoku (boiled, concentrated and cooled agar in water), jelly, sponge cake (pao de Castella), and candies; various western-type confectioneries such as bread, biscuits, crackers, cookies, pie, pudding, buttercream, custardcream, chou a la creme, waffle, sponge cake, doughnut, chocolate, chewing gum, caramel, and candies; cold confectioneries such as ice cream and sherbet; syrups such as syrups for fruit dipping and ice syrups; pastes such as flower paste, peanut paste and fruit paste; processed foods of fruit and vegetables, such as jam, marmalade, fruit-dipped syrups, and sugar-coated fruits; cereal-processed foods such as breads, noodles, cooked rice, and artificial meat; pickles such as pickles for curry on rice, radish pickles in sweet vinegar, thinly sliced radish pickles in sweet vinegar, and rakkyo (a kind of garlic) pickles; pickle seasoning mix such as seasoning mix for radish pickle and seasoning mix for Chinese cabbage pickle; cattle products such as ham and sausage; fish products such as fish ham, fish sausage, fish cake, bar-shaped fish cake with holes, and tempura; various tidbits such as sea urchin, squad sprinkled with salt, kelp seasoned with vinegar, dried and sliced squad, mirin-seasoned, dried fugu (globefish); foods boiled down in soy sauce and sugar such as those produced from seaweed (nori), vegetables harvested on mountainous regions, dried squad, small fishes and shellfish; household dishes such as boiled bean, potato salad, and rolled kelp; dairy products; bottled or canned fish, cattle meat, fruit and vegetable; liquors and wines such as synthetic liquor, fruit wine, western-style liquors, and liquors; refreshing beverages such as coffee, cocoa, juice, carbonate drinks, lactate drinks, and lactic acid bacterium drinks; premix powders such as pudding mix, and hot cake mix; instant foods and drinks such as instant juice, instant coffee, instant adzuki-bean soup, and instant soups.

Drinks to be essentially at low calories particularly include for example carbonate drinks such as cola, sport drinks, fruit drinks, dairy drinks, and tea drinks. It can be said that in particular, carbonate drinks causing obesity at excess intake are the most suitable targets.

Examples of pharmaceutical products given with sweetness include sugar-coated tablets. Since the taste and odor of drugs in the sugar-coated tablets are masked with the sugar coating layer on the surface, the sugar-coated tablets are readily administered and have good appearance. Additionally because such sugar-coated tablets have a moisture-proof property, the sugar-coated tablets have been used widely in pharmaceutical products such as solid pharmaceutical preparations and foods. Such sugar-coated tablets can be produced generally by coating a sucrose solution on a tablet and drying the resulting tablet, and repeating the process to complete the formation of the sugar coating layer, preparing the tablet shape to an ellipse shape, coating a wax thereon and polishing the surface for gloss.

As the sucrose solution for sugar coating, generally, there is used sucrose as a base material to which binders such as gelatin, gum Arabic and polyvinyl pyrrolidone are preliminarily added so as to enhance the intensity of the sugar coating layer of the resulting sugar-coated tablet. If necessary, further, powders such as talc, calcium sulfate, calcium phosphate and precipitated calcium carbonate are added. Drugs with strong odor and with strong bitterness hardly prepared as oral agents are modified as sugar-coated tablets. In place of sugar for use in the sugar-coated tablets or in addition to the sugar, the lower-calorie sweetener of the invention may be used. As well known, additionally, so many drugs hardly administrable exist. Because barium has unique odor and taste, barium is modified in a form readily administrable with some additives. But such barium preparation may further be modified possibly. So as to prepare more readily administrable liquid pharmaceutical preparations and auxiliary diagnostic agents by giving sweetness thereto, the low-calorie sweetener and/or the sweetener giving refreshing feel in the oral cavity in accordance with the invention may possible be used. Some drugs are in powders. Hence, such drugs may be modified as readily administrable preparations by adding the low-calorie sweetener and/or the sweetener giving refreshing feel in the oral cavity in accordance with the invention thereto.

In case of giving sweetness to an oral composition, the oral composition can be prepared according to general methods by blending the low-calorie sweetener in accordance with the invention. The low-calorie sweetener in accordance with the invention is the most suitable for giving taste to toothpaste, tooth liquid, and mouthwash. In accordance with the invention, the term "oral composition" means a composition to be masticated or to be used for gargling and includes for example foods such as chewing gum, candies, confectionary tablets, and confectionary films; and pharmaceutical products such as toothpaste, tooth liquid and mouthwash.

The invention is now described in more detail in Comparative Examples and Examples. However, the invention is never limited to these Examples.

EXAMPLE 1

According to the formulations in table 1, samples were prepared by dissolving erythritol and D-psicose in water (Comparative Examples 1 and 2 and Test Examples 1 through 5).

Herein, D-psicose used was supplied from the Rare Sugar Research Center, the National University Corporation Kagawa University.

TABLE 1

Formulations (unit: g)

| | Comparative Examples | | Test Examples | | | | |
|---|---|---|---|---|---|---|---|
| | 1 | 2 | 1 | 2 | 3 | 4 | 5 |
| D-Psicose | 16.7 | — | 0.835 | 5.0 | 8.33 | 11.67 | 15.8 |
| Erythritol | — | 12.5 | 11.88 | 8.75 | 6.25 | 3.75 | 0.63 |
| Water | To 100 | To 100 | To 100 | To 100 | To 100 | To 100 | To 100 |

Five panelists drank the samples in the Comparative Examples 1 and 2 and the Test Examples 1 through 5 for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the sweeteners are shown in Table 2.

TABLE 2

Results of sensory test of sweeteners

|  | Slow start of the sweetness in the former stage | Balance of sweetness | Heavy taste |
|---|---|---|---|
| Comparative Example 1 | 1 | 2 | 7 |
| Comparative Example 2 | 7 | 1 | 1 |
| Test Example 1 | 6 | 3 | 2 |
| Test Example 2 | 5 | 5 | 3 |
| Test Example 3 | 4 | 6 | 4 |
| Test Example 4 | 3 | 7 | 5 |
| Test Example 5 | 2 | 4 | 6 |

The results in Table 2 show that compared with Comparative Example 1 with no combination, the sweeteners of the invention are improved in terms of the start of the sweetness in the former stage and the balance in sweetness in the Test Examples 2 through 4; compared with Comparative Example 2, the sweeteners of the invention are improved in terms of the balance in sweetness and the heavy taste in the Test Examples 2 through 4.

EXAMPLE 2

According to the formulations in table 3, samples were prepared by dissolving xylitol and D-psicose in water.

Five panelists drank the samples in the Comparative Examples 1 and 2 and the Present Inventions (Test Examples 1 through 5) for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the sweeteners are shown in Table 4.

TABLE 4

Results of sensory test of sweeteners

|  | Slow start of the sweetness in the former stage | Balance of sweetness | Heavy taste |
|---|---|---|---|
| Comparative Example 1 | 1 | 2 | 1 |
| Comparative Example 2 | 7 | 1 | 7 |
| Test Example 1 | 2 | 4 | 2 |
| Test Example 2 | 3 | 6 | 3 |
| Test Example 3 | 4 | 7 | 4 |
| Test Example 4 | 5 | 5 | 5 |
| Test Example 5 | 6 | 3 | 6 |

The results in Table 4 show that compared with Comparative Example 1 with no combination, the sweeteners of the invention are improved in terms of the start of the sweetness in the former stage, the balance in sweetness and the heavy taste in the Test Examples 2 through 4; compared with Comparative Example 2, the sweeteners of the invention are improved in terms of the balance in sweetness in the Test Examples 2 through 4.

EXAMPLE 3

According to the formulations in table 5, samples were prepared by dissolving aspartame and D-psicose in water.

TABLE 3

Formulations (unit: g)

|  | Comparative Examples | | Test Examples | | | | |
|---|---|---|---|---|---|---|---|
|  | 1 | 2 | 1 | 2 | 3 | 4 | 5 |
| D-Psicose | 16.67 | — | 0.83 | 5.0 | 8.33 | 11.67 | 15.83 |
| Xylitol | — | 16.67 | 15.83 | 11.67 | 8.33 | 5.0 | 0.83 |
| Water | To 100 | To 100 | To 100 | To 100 | To 100 | To 100 | To 100 |

TABLE 5

| | Formulations (unit: g) | | | | | | |
|---|---|---|---|---|---|---|---|
| | Comparative Examples | | Test Examples | | | | |
| | 1 | 2 | 1 | 2 | 3 | 4 | 5 |
| D-Psicose | 16.67 | — | 0.83 | 5.0 | 8.33 | 11.67 | 15.83 |
| Aspartame | — | 0.05 | 0.0475 | 0.035 | 0.025 | 0.015 | 0.0025 |
| Water | To 100 | To 100 | To 100 | To 100 | To 100 | To 100 | To 100 |

Five panelists drank the samples in the Comparative Examples 1 and 2 and the Present Inventions (Test Examples 1 through 5) for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the sweeteners are shown in Table 6.

TABLE 6

| | Results of sensory test of sweeteners | | |
|---|---|---|---|
| | Slow start of the sweetness in the former stage | Balance of sweetness | Heavy taste |
| Comparative Example 1 | 7 | 2 | 7 |
| Comparative Example 2 | 1 | 1 | 1 |
| Test Example 1 | 2 | 4 | 2 |
| Test Example 2 | 3 | 5 | 3 |
| Test Example 3 | 4 | 6 | 4 |
| Test Example 4 | 5 | 7 | 5 |
| Test Example 5 | 6 | 3 | 6 |

The results in Table 6 show that compared with Comparative Example 1 with no combination, the sweeteners of the invention are improved in terms of the balance in sweetness in the Test Examples 2 through 4; compared with Comparative Example 2, the sweeteners of the invention are improved in terms of the start of the sweetness in the former stage, the balance in sweetness and the heavy taste in the Test Examples 2 through 4.

EXAMPLE 4

According to the formulations in table 7, samples were prepared by dissolving acesulfame K and D-psicose in water.

TABLE 7

| | Formulations (unit: g) | | | | | | |
|---|---|---|---|---|---|---|---|
| | Comparative Examples | | Test Examples | | | | |
| | 1 | 2 | 1 | 2 | 3 | 4 | 5 |
| D-Psicose | 16.67 | — | 0.83 | 5.0 | 8.33 | 11.67 | 15.83 |
| Acesulfame K | — | 0.05 | 0.0475 | 0.035 | 0.025 | 0.015 | 0.0025 |
| Water | To 100 | To 100 | To 100 | To 100 | To 100 | To 100 | To 100 |

Five panelists drank the samples in the Comparative Examples 1 and 2 and the Present Inventions (Test Examples 1 through 5) for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the sweeteners are shown in Table 8.

TABLE 8

| | Results of sensory test of sweeteners | | |
|---|---|---|---|
| | Slow start of the sweetness in the former stage | Balance of sweetness | Heavy taste |
| Comparative Example 1 | 1 | 2 | 7 |
| Comparative Example 2 | 7 | 1 | 1 |
| Test Example 1 | 6 | 3 | 2 |
| Test Example 2 | 5 | 5 | 3 |
| Test Example 3 | 4 | 6 | 4 |
| Test Example 4 | 3 | 7 | 5 |
| Test Example 5 | 2 | 4 | 6 |

The results in Table 8 show that compared with Comparative Example 1 with no combination, the sweeteners of the invention are improved in terms of the start of the sweetness in the former stage and the balance in sweetness in the Test Examples 2 through 4; compared with Comparative Example 2, the sweeteners of the invention are improved in terms of the balance in sweetness and the heavy taste in the Test Examples 2 through 4.

EXAMPLE 5

According to the formulations in table 9, samples were prepared by dissolving maltitol, erythritol and D-psicose in water.

TABLE 9

Formulations (unit: g)

| | Comparative Examples | | Test Examples | | | |
|---|---|---|---|---|---|---|
| | 1 | 2 | 1 | 2 | 3 | 4 |
| D-Psicose | 16.67 | — | 0.66 | 6.67 | 10.0 | 16.0 |
| Maltitol | — | 6.25 | 6.0 | 3.75 | 2.5 | 0.25 |
| Erythritol | — | 6.25 | 6.0 | 3.75 | 2.5 | 0.25 |
| Water | To 100 | To 100 | To 100 | To 100 | To 100 | To 100 |

Five panelists drank the samples in the Comparative Examples 1 and 2 and the Present Inventions (Test Examples 1 through 4) for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the sweeteners are shown in Table 10.

TABLE 10

Results of sensory test of sweeteners

| | Slow start of the sweetness in the former stage | Balance of sweetness | Heavy taste |
|---|---|---|---|
| Comparative Example 1 | 1 | 1 | 6 |
| Comparative Example 2 | 6 | 2 | 1 |
| Test Example 1 | 5 | 4 | 2 |
| Test Example 2 | 4 | 6 | 3 |
| Test Example 3 | 3 | 5 | 4 |
| Test Example 4 | 2 | 3 | 5 |

The results in Table 10 show that compared with Comparative Example 1 with no combination, the sweeteners of the invention are improved in terms of the start of the sweetness in the former stage and the balance in sweetness in the Test Examples 2 and 3; compared with Comparative Example 2, the sweeteners of the invention are improved in terms of the balance in sweetness and the heavy taste in the Test Examples 2 and 3.

EXAMPLE 6

According to the formulations in table 11, samples were prepared by dissolving acesulfame K, Sucralose and D-psicose in water.

TABLE 11

Formulations (unit: g)

| | Comparative Examples | | Test Examples | | | |
|---|---|---|---|---|---|---|
| | 1 | 2 | 1 | 2 | 3 | 4 |
| D-Psicose | 16.67 | — | 0.667 | 6.67 | 10 | 16 |
| Acesulfame K | — | 0.025 | 0.024 | 0.015 | 0.01 | 0.001 |
| Sucralose | — | 0.0083 | 0.008 | 0.005 | 0.0033 | 0.00033 |
| Water | To 100 | To 100 | To 100 | To 100 | To 100 | To 100 |

Five panelists drank the samples in the Comparative Examples 1 and 2 and the Present Inventions (Test Examples 1 through 4) for sensory evaluation.

The panel was composed of five males with refined taste in age 30 to 40 years old.

The individual panelists scored and ranked the intensity and level in terms of the slow start of the sweetness in the former stage, the good balanced sweetness and the heavy taste in the individual samples (in other words, greater numerical scores show higher ranks). The results of the sensory test of the sweeteners are shown in Table 12.

TABLE 12

Results of sensory test of sweeteners

|  | Slow start of the sweetness in the former stage | Balance of sweetness | Heavy taste |
|---|---|---|---|
| Comparative Example 1 | 1 | 1 | 6 |
| Comparative Example 2 | 6 | 2 | 1 |
| Test Example 1 | 5 | 3 | 2 |
| Test Example 2 | 4 | 5 | 3 |
| Test Example 3 | 3 | 6 | 4 |
| Test Example 4 | 2 | 4 | 5 |

The results in Table 12 show that compared with Comparative Example 1 with no combination, the sweeteners of the invention are improved in terms of the start of the sweetness in the former stage and the balance in sweetness in the Test Examples 2 and 3; compared with Comparative Example 2, the sweeteners of the invention are improved in terms of the balance in sweetness and the heavy taste in the Test Examples 2 and 3.

EXAMPLE 7

According to the formulations in table 13, samples were prepared by dissolving acesulfame K, Sucralose, erythritol and D-psicose in water.

TABLE 13

Formulations (unit: g)

|  | Comparative Examples | | Test Examples | | | |
|---|---|---|---|---|---|---|
|  | 1 | 2 | 1 | 2 | 3 | 4 |
| D-Psicose | 16.67 | — | 0.667 | 4.167 | 6.67 | 15.67 |
| Acesulfame K | — | 0.0167 | 0.016 | 0.0125 | 0.01 | 0.001 |
| Sucralose | — | 0.0167 | 0.0053 | 0.0125 | 0.01 | 0.00033 |
| Erythritol | — | 4.167 | 4.0 | 3.125 | 2.5 | 0.25 |
| Water | To 100 | To 100 | To 100 | To 100 | To 100 | To 100 |

Five panelists drank the samples in the Comparative Examples 1 and 2 and the Present Inventions (Test Examples 1 through 4) for sensory evaluation.

The panel was composed of five males with refined taste in age 30 to 40 years old.

The individual panelists scored and ranked the intensity and level in terms of the slow start of the sweetness in the former stage, the good balanced sweetness and the heavy taste in the individual samples (in other words, greater numerical scores show higher ranks). The results of the sensory test of the sweeteners are shown in Table 14.

TABLE 14

Results of sensory test of sweeteners

|  | Slow start of the sweetness in the former stage | Balance of sweetness | Heavy taste |
|---|---|---|---|
| Comparative Example 1 | 1 | 1 | 6 |
| Comparative Example 2 | 6 | 2 | 1 |
| Test Example 1 | 5 | 3 | 2 |
| Test Example 2 | 4 | 6 | 3 |
| Test Example 3 | 3 | 5 | 4 |
| Test Example 4 | 2 | 4 | 5 |

The results in Table 14 show that compared with Comparative Example 1 with no combination, the sweeteners of the invention are improved in terms of the start of the sweetness in the former stage and the balance in sweetness in the Test Examples 2 and 3; compared with Comparative Example 2, the sweeteners of the invention are improved in terms of the balance in sweetness and the heavy taste in the Test Examples 2 and 3.

EXAMPLE 8

According to the formulations in table 15, sour drinks were prepared.

TABLE 15

| Formulations (unit: g) | Comparative Examples | | Test Examples | | |
| --- | --- | --- | --- | --- | --- |
| | 1 | 2 | 1 | 2 | 3 |
| D-Psicose | 13.33 | — | 3.33 | 6.67 | 10 |
| Stevia | — | 0.02 | 0.015 | 0.01 | 0.005 |
| Erythritol | — | 5 | 3.75 | 2.5 | 1.25 |
| Citric acid | 0.1 | 0.1 | 0.1 | 0.1 | 0.1 |
| Sodium citrate | 0.02 | 0.02 | 0.02 | 0.02 | 0.02 |
| Potassium chloride | 0.02 | 0.02 | 0.02 | 0.02 | 0.02 |
| Flavor | 0.1 | 0.1 | 0.1 | 0.1 | 0.1 |
| Water | To 100 | To 100 | To 100 | To 100 | To 100 |

Five panelists drank the samples in the Comparative Examples 1 and 2 and the Present Inventions (Test Examples 1 through 3) for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the drinks are shown in Table 16.

TABLE 16

| Results of sensory test of drinks | Slow start of the sweetness in the former stage | Balance of sweetness | Heavy taste |
| --- | --- | --- | --- |
| Comparative Example 1 | 1 | 1 | 5 |
| Comparative Example 2 | 5 | 2 | 1 |
| Test Example 1 | 4 | 3 | 2 |
| Test Example 2 | 3 | 5 | 3 |
| Test Example 3 | 2 | 4 | 4 |

The results in Table 16 show that compared with Comparative Example 1 with no combination, the drinks using the sweeteners of the invention are improved in terms of the start of the sweetness in the former stage and the balance in sweetness; compared with Comparative Example 2, the drinks are improved in terms of the balance in sweetness and the heavy taste.

EXAMPLE 9

According to the formulations in table 17, cold confectioneries were prepared by routine methods.

TABLE 17

| Formulations (unit: g) | Comparative Example | | Test Examples | | | | |
| --- | --- | --- | --- | --- | --- | --- | --- |
| | 1 | 2 | 1 | 2 | 3 | 4 | 5 |
| ⅕ orange juice | 4.6 | 4.6 | 4.6 | 4.6 | 4.6 | 4.6 | 4.6 |
| D-Psicose | 30.0 | — | 5 | 10 | 15 | 20 | 25 |
| Maltitol | — | 15.0 | 12.5 | 10 | 7.5 | 5 | 2.5 |
| Sucralose | — | 0.01 | 0.0083 | 0.0067 | 0.005 | 0.0033 | 0.0017 |
| Fiber sol 2 | 6.3 | 6.3 | 6.3 | 6.3 | 6.3 | 6.3 | 6.3 |
| Palm oil | 1.0 | 1.0 | 1.0 | 1.0 | 1.0 | 1.0 | 1.0 |
| Emulsifying agent | 0.1 | 0.1 | 0.1 | 0.1 | 0.1 | 0.1 | 0.1 |
| Stabilizer | 0.3 | 0.3 | 0.3 | 0.3 | 0.3 | 0.3 | 0.3 |
| Flavor | 0.1 | 0.1 | 0.1 | 0.1 | 0.1 | 0.1 | 0.1 |
| Water | To 100 | To 100 | To 100 | To 100 | To 100 | To 100 | To 100 |

Five panelists drank the samples in the Comparative Examples 1 and 2 and the Present Inventions (Test Examples 1 through 5) for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the cold confectioneries are shown in Table 18.

TABLE 18

Results of sensory test of cold confectionaries

|  | Slow start of the sweetness in the former stage | Balance of sweetness | Heavy taste |
| --- | --- | --- | --- |
| Comparative Example 1 | 1 | 1 | 7 |
| Comparative Example 2 | 7 | 2 | 1 |
| Test Example 1 | 2 | 3 | 2 |
| Test Example 2 | 3 | 4 | 3 |
| Test Example 3 | 4 | 6 | 4 |
| Test Example 4 | 5 | 7 | 5 |
| Test Example 5 | 6 | 5 | 6 |

The results in Table 18 show that compared with Comparative Example 1 with no combination, the cold confectioneries using the sweeteners of the invention are improved in terms of the start of the sweetness in the former stage and the balance in sweetness; compared with Comparative Example 2, the cold confectioneries are improved in terms of the balance in sweetness and the heavy taste.

EXAMPLE 10

According to the formulations in table 19, yogurts were prepared.

TABLE 19

Formulations (unit: g)

|  | Comparative Example | | Test Examples | | |
| --- | --- | --- | --- | --- | --- |
|  | 1 | 2 | 1 | 2 | 3 |
| D-Psicose | 10.0 | — | 2.5 | 5.0 | 7.5 |
| Acesulfame K | — | 0.03 | 0.0225 | 0.015 | 0.0075 |
| Defatted milk powder | 9.0 | 9.0 | 9.0 | 9.0 | 9.0 |
| Fiber sol 2 | 3.0 | 3.0 | 3.0 | 3.0 | 3.0 |
| Gelatin | 0.3 | 0.3 | 0.3 | 0.3 | 0.3 |
| Agar | 0.2 | 0.2 | 0.2 | 0.2 | 0.2 |
| Flavor | 0.1 | 0.1 | 0.1 | 0.1 | 0.1 |
| Water | 71.4 | 81.37 |  |  |  |
| Starter | 6.0 | 6.0 | 6.0 | 6.0 | 6.0 |

Five panelists drank the samples in the Comparative Examples 1 and 2 and the Present Inventions (Test Examples 1 through 3) for sensory evaluation.

The panel was composed of five males with refined taste in age 30 to 40 years old.

The individual panelists scored and ranked the intensity and level in terms of the start of the sweetness in the former stage, the good balanced sweetness and the heavy taste in the individual samples (in other words, greater numerical scores show higher ranks). The results of the sensory test of the yogurt are shown in Table 20.

TABLE 20

Results of sensory test of yogurts

|  | Slow start of the sweetness in the former stage | Balance of sweetness | Heavy taste |
| --- | --- | --- | --- |
| Comparative Example 1 | 1 | 1 | 5 |
| Comparative Example 2 | 5 | 2 | 1 |
| Test Example 1 | 4 | 3 | 2 |
| Test Example 2 | 3 | 5 | 3 |
| Test Example 3 | 2 | 4 | 4 |

The results in Table 20 show that compared with Comparative Example 1 with no combination, the yogurts using the sweeteners of the invention are improved in terms of the start of the sweetness in the former stage and the balance in sweetness; compared with Comparative Example 2, the yoghurts are improved in terms of the balance in sweetness and the heavy taste.

EXAMPLE 11

Sensory Test of Refreshing Feel

It is understood that refreshing feel differs from the profile of dissolution heat actually measured with a meter, because refreshing feel depends on the particle size of a composition and the dissolution property thereof and also depends on the sweetness level, the sharpness in sweetness and the bodily taste of a food composition. Therefore, xylitol as a sugar alcohol actually giving refreshing feel and sucrose as a general sweetener as a comparison were used for a sensory test in humans.

Six panelists drank 0.6 g of each of sugars, and ranked and scored the refreshing feel in three grades. (In other words, a smaller numerical score represents a higher rank.) The panel was composed of six males and females with refined taste in 20 to 50 years old. The results of the sensory test are shown in Table 21.

TABLE 21

Results of D-psicose sensory test

|  | Refreshing feel in mouth |
| --- | --- |
| Sucrose | 3 |
| D-Psicose | 2 |
| Xylitol | 1 |

The results in table 21 apparently show that D-psicose kept at the anhydrous state enhanced the oral refreshing feel when the D-psicose absorbed water. The dissolution heat of D-psicose was actually measured. The endothermic heat during dissolution was 27.4 cal/g. It was first revealed that D-psicose was characterized by such high negative dissolution heat. The dissolution heat was 4936 cal/mol per mol, and it was shown that D-psicose exerted an action almost similar to that of erythritol for use as an endothermic agent, which was at 5239 cal/mol. The sweetness of xylitol is closer to the sweetness of sucrose, than that of D-psicose. The sharp sweetness of xylitol may have influenced the evaluation of the oral refreshing feel.

EXAMPLE 12

Then, a sensory test was done so as to verify whether or not the co-existence of xylitol with highly acclaimed refreshing feel with D-psicose could retain the refreshing feel and improve the balance in sweetness.

Six panelists ingested 0.6 g xylitol, 0.6 g D-psicose, and 0.4 g xylitol+0.2 g D-psicose, and then ranked the refreshing feel thereof. In three grades, the refreshing feel was scored. Simultaneously, the panelists ranked the sweetness in the order of preferable sweetness in three grades. The panel was composed of six males and females with refined taste in 20 to 50 years old. The results of the sensory test are shown in table 22.

TABLE 22

Results of sensory test of D-psicose

|  | Oral refreshing feel | Preferable sweetness |
|---|---|---|
| D-Psicose | 3 | 2 |
| Xylitol | 1 | 3 |
| D-Psicose + Xylitol | 2 | 1 |

Results in Table 22 show that the combined use of D-psicose and xylitol could retain the refreshing feel thereof to produce a preferable sweetness. It was shown that the combined use of D-psicose with the sugar alcohol could retain the refreshing feel of D-psicose and could also produce a preferable sweetness.

EXAMPLE 13

As food materials bringing about refreshing feel, there have been known stimulant substances such as menthol, mint oil and peppermint oil. It is suggested that raw materials causing stimulation when humans ingest the raw materials may give preferable influences to the sweetness and refreshing feel of D-psicose.

5 mg of menthol was added to 1 g of the solid sweetener [D-psicose+xylitol (2:1)] in accordance with the invention. Then, the resulting mixture was ingested in trials, so that the refreshing feel was enhanced while the resulting sweetness was preferable. The combination thereof is preferably used for candies for throat soothing, gums, edible films, and oral compositions. The sweetener of the invention to which menthol is preliminarily added was in good taste balance compared with menthol added to D-psicose alone.

EXAMPLE 14

Chewing Gum Composition

According to the composition list in table 23 (chewing gum), a chewing gum was prepared, to enclose the solid sweetener with the refreshing action in accordance with the invention [0.5 g of the sweetener of the invention (D-psicose+xylitol (2:1) per 2 g chewing gum).

TABLE 23

| Chewing gum | |
|---|---|
| Ingredient | Ratio (%) |
| Gum base 1 | 30.0 |
| Gum base 2 | 30.0 |
| Glutinous starch syrup | Appropriate ratio |
| pH adjuster | Appropriate ratio |
| Glycerin | 3.5 |
| Citric acid | 3.5 |
| Lemon flavor | 3.0 |
| Green tea extract | 3 |
| Yellow dye from safflower | 0.3 |

EXAMPLE 15

Edible Film Composition

According to the composition list in table 24 (water-soluble film), an edible film was prepared, on which the sweetener with the refreshing action was sprinkled in powder [0.5 g of the sweetener of the invention (D-psicose+xylitol 2:1) per 2 g edible film].

TABLE 24

| Edible film | |
|---|---|
| Ingredient | Ratio (%) |
| Film-forming agent | 60.0 |
| Hydrocolloid | 3.0 |
| Plasticizer | 20.0 |
| Flavor | 10.0 |
| Sugar alcohol | Appropriate ratio |

Through the use of the crystalline D-psicose as a composition, the chewing gum and the edible film in Examples 14 and 15, respectively can get refreshing feel and fresh sweetness. It was shown that more tasteful chewing gum or edible film was obtained with the sweetener as a combination of D-psicose and a sugar alcohol in accordance with the invention.

Existing pharmaceutical ingredients for common use in a mouthwash composition, for example cetylpyridinium chloride, triclosan, cineole, thymol, zinc chloride, methyl salicylate and vitamin E can be added to the edible film.

INDUSTRIAL APPLICABILITY

It is a very important issue to develop a measure for reducing the intake of sucrose as one of major caloric sources and an important sweetener for cooking or to develop a sweetener as an alternative sucrose, which is at a low calorie and gives taste comparable to that of sucrose. Therefore, it can be provided a low-calorie sweetener and/or a sweetener giving refreshing feel in the oral cavity, by improving the problems of D-psicose, such as the slow start of the sweetness of D-psicose and the heavy taste thereof when used at a large amount to modify the taste, so that the resulting sweeteners can widely be used in foods and drinks like sucrose.

The invention claimed is:

1. A method of producing a D-psicose-containing sweetener having a taste comparable to a taste of sucrose, the method comprising:
   combining D-psicose as a main component with at least one selected from the group consisting of erythritol and a *stevia* sweetener,
   wherein the sweetener comprises 30 parts or more of erythritol in relation to 100 parts of D-psicose, or the sweetener comprises 0.05-1.5 parts of the *stevia* sweetener in relation to 100 parts of D-psicose, a total amount of the erythritol and the *stevia* sweetener being less than 100 parts in relation to 100 parts of D-psicose, such that the taste of the D-psicose-containing sweetener is comparable to the taste of sucrose.

2. The method according to claim 1, wherein the sweetener comprises erythritol.

3. The method according to claim 1, wherein the sweetener comprises the *stevia* sweetener.

4. A method comprising adding the D-psicose-containing sweetener according to claim 1 to a food or drink to produce the food or drink containing the D-psicose-containing sweetener.

5. A sweetener having a taste comparable to a taste of sucrose, the sweetener comprising:
   D-psicose as a main component; and
   at least one selected from the group consisting of erythritol and a *stevia* sweetener,
   wherein the sweetener comprises 30 parts or more of erythritol in relation to 100 parts of D-psicose, or the sweetener comprises 0.05-1.5 parts of the *stevia* sweetener in relation to 100 parts of D-psicose, a total amount of the erythritol and the *stevia* sweetener being less than 100 parts in relation to 100 parts of D-psicose, such that the taste of the D-psicose-containing sweetener is comparable to the taste of sucrose.

6. The sweetener according to claim 5, wherein the sweetener comprises the *stevia* sweetener.

7. The sweetener according to claim 5, wherein the sweetener comprises erythritol.

8. A food or a drink, comprising the sweetener according to claim 5.

* * * * *